United States Patent
Andrighetto et al.

(10) Patent No.: US 12,360,097 B2
(45) Date of Patent: Jul. 15, 2025

(54) METHOD AND APPARATUS OF PREPARING OF A SILAGE GOOD AND ENSILING PROCESS

(71) Applicants: KWS SAAT SE & CO. KGAA, Einbeck (DE); UNIVERSITA DEGLI STUDI DI PADOVA, Padua (IT)

(72) Inventors: Igino Andrighetto, Legnaro (IT); Giorgio Marchesini, Legnaro (IT); Lorenzo Serva, Legnaro (IT); Matteo Gazziero, Legnaro (IT); Sandro Tenti, Legnaro (IT); Massimo Mirisola, Legnaro (IT); Elisabetta Garbin, Legnaro (IT); Barbara Contiero, Legnaro (IT); Daniel Grandis, Monselice (IT)

(73) Assignees: KWS SAAT SE & CO. KGAA, Einbeck (DE); UNIVERSITA DEGLI STUDI DI PADOVA, Padua (IT)

( * ) Notice: Subject to any disclaimer, the term of this patent is extended or adjusted under 35 U.S.C. 154(b) by 868 days.

(21) Appl. No.: 17/253,371

(22) PCT Filed: Jun. 21, 2019

(86) PCT No.: PCT/EP2019/066545
§ 371 (c)(1),
(2) Date: Dec. 17, 2020

(87) PCT Pub. No.: WO2019/243615
PCT Pub. Date: Dec. 26, 2019

(65) Prior Publication Data
US 2021/0255160 A1    Aug. 19, 2021

(30) Foreign Application Priority Data
Jun. 22, 2018 (EP) .................... 18425048

(51) Int. Cl.
*G01N 33/02* (2006.01)
*A23K 10/10* (2016.01)
(Continued)

(52) U.S. Cl.
CPC ............. *G01N 33/02* (2013.01); *A23K 10/10* (2016.05); *A23K 10/16* (2016.05); *A23K 30/15* (2016.05); *A23K 30/18* (2016.05); *A23N 17/008* (2013.01)

(58) Field of Classification Search
CPC ................. G01N 33/02; G01N 33/025; A23K 10/12–18; A23K 10/30;
(Continued)

(56) References Cited

U.S. PATENT DOCUMENTS 4,292,331 A * 9/1981 Ostre ..................... A23K 30/18
426/52
4,528,199 A * 7/1985 Moon .................... A23K 30/18
435/857
(Continued)

FOREIGN PATENT DOCUMENTS

CN    101516209 A    8/2009
CN    103750077 A    4/2014
(Continued)

OTHER PUBLICATIONS

Martinez-Fernandez et al., "Modelling a quantitative ensilability index adapted to forages from wet temperature areas", Spanish Journal of Agricultural Research 2013, pp. 455-462 (Year: 2013).*
(Continued)

*Primary Examiner* — Drew E Becker
*Assistant Examiner* — Austin Parker Taylor
(74) *Attorney, Agent, or Firm* — Troutman Pepper Locke LLP

(57) ABSTRACT

The invention refers to a method of preparing of a silage good having improved quality, to an ensiling process employing the method or the silage good, and an apparatus of preparing of a silage good having improved quality. The method includes applying a first model on determined
(Continued)

parameters to determine an ensilability index number and applying a second model on the determined parameters to determine a retention index number for a harvested good. The method can further include determining types and amounts of ensiling additives to be added to the harvested good for controlling the ensiling process depending on the ensilability index number and the retention index number and supplying the determined additives to the harvested good to obtain the silage good.

16 Claims, 5 Drawing Sheets

(51) Int. Cl.
*A23K 10/16* (2016.01)
*A23K 30/15* (2016.01)
*A23K 30/18* (2016.01)
*A23N 17/00* (2006.01)

(58) Field of Classification Search
CPC . A23K 30/00–20; A23N 17/008; A01F 25/00; A01F 25/16; B02B 1/00; B02B 1/08; C12M 21/00; C12M 21/02; C12M 21/04; C12M 21/12; C12M 21/16; C12M 21/18
USPC ........................................ 426/49, 52, 53, 54
See application file for complete search history.

(56) References Cited

U.S. PATENT DOCUMENTS

| | | | | |
|---|---|---|---|---|
| 8,633,820 | B2* | 1/2014 | Jonsson | H04L 67/12 |
| | | | | 426/531 |
| 2008/0138463 | A1* | 6/2008 | Chan | C12N 1/20 |
| | | | | 435/252.9 |
| 2013/0190061 | A1* | 7/2013 | Kirchbeck | A01D 43/14 |
| | | | | 460/1 |
| 2018/0080887 | A1* | 3/2018 | Bajema | G01N 33/02 |
| 2018/0322436 | A1* | 11/2018 | Sotiroudas | G01N 33/0075 |

FOREIGN PATENT DOCUMENTS

| | | |
|---|---|---|
| WO | 2010/015579 A1 | 2/2010 |
| WO | 2013/045931 A1 | 4/2013 |

OTHER PUBLICATIONS

Goeser et al., "Forage fermentation product measures are related to dry matter loss through meta-analysis", The Professional Animal Scientist 31 ( 2015 ):137-145 (Year: 2015).*
Andrighetto et al., "Proposal and validation of new indexes to evaluate maize silage fermentative quality in lab-scale ensiling conditions through the use of a receiver operating characteristic analysis", Animal Feed Science and Technology, 2018, vol. 242, pp. 31-40.
International Search Report and Written Opinion issued in Application No. PCT/EP2019/066545 dated Sep. 4, 2019.
Jatkauskas et al., "Evaluation of fermentation parameters, microbiological composition and aerobic stability of grass and whole crop maize silages treated with microbial inoculants", Zemdirbyste-Agriculture, vol. 100, No. 2, 2013, pp. 143-150.
Sanchez et al., "Assessment of Ensilability and Chemical Composition of Canola and Alfalfa Forages with or without Microbial Inoculation", Indian J. Agric. Res., vol. 48, No. 6, 2014, pp. 421-428.
Martinez-Femandez et al., "Modelling a quantitative ensilability index adapted to forages from wet temperate areas", Spanish Journal of Agricultural Research, 2013, vol. 11, No. 2, pp. 455-462.

* cited by examiner

METHOD AND APPARATUS OF PREPARING OF A SILAGE GOOD AND ENSILING PROCESS

CROSS-REFERENCE TO RELATED APPLICATIONS

This application is a U.S. National Phase of International Patent Application No. PCT/EP2019/066545, filed on Jun. 21, 2019, which claims priority to European Application No. 18425048.8, filed Jun. 22, 2018. The entire contents of these applications are incorporated herein by reference in their entirety.

The invention refers to a method of preparing of a silage good having improved quality, to an ensiling process employing the method or the silage good, and an apparatus of preparing of a silage good having improved quality.

BACKGROUND OF THE INVENTION

Maize silage is one of the most widely used feed in cattle rations in a great part of the world. Although the nutritional composition of silage, which is usually characterized by its chemical composition, dry matter content, crude protein, starch, fibre, and nutrients digestibility, is of primary importance to optimize animal performance, it is generally accepted that the quality of the fermentation during the ensiling process and its aerobic stability are important as well. In fact, a silage that has undergone an abnormal fermentation has a lower nutritional value, and is often rejected by animals, leading to reduced dry matter intake and lower performance. The quality of fermentation occurring during the ensiling process can be determined by analysis of the pH and the concentration of a wide range of fermentation products such as lactate, acetate, propionate, butyrate, isobutyrate, ethanol, mannitol, and ammonia. However, each of these parameters only give information on a certain aspect of fermentation. Thus, in order to assess whether a fermentation was qualitatively better than another, quality index scores such as the Flieg-Zimmer's score, the German agricultural society's (DLG) and Vanbelle's scores, or the quality indexes I1-I6 as previously described in Igino Andrighetto et al. (Andrighetto I et al. (2018), Proposal and validation of new indexes to evaluate maize silage fermentative quality in lab-scale ensiling conditions through the use of a receiver operating characteristic analysis", Anim. Feed Sci. Techno. 242:31-40) had to be established that take into account the weight of the different parameters.

These index scores, however, only provide information about the silage quality after fermentation and do not allow any modification or improvement of the ensiling process.

It was therefore an object of the present invention to provide a method that allows the farmer to predict whether freshly harvested crops, preferably maize, can be transformed into a good silage in the course of fermentation. Such a method would allow the farmer to modify the ensiling process based on the chemical composition of freshly harvested crops to improve the quality of the silage product. It is therefore an intention of the present invention to provide a method for determining whether freshly harvested crops, preferably maize, can be transformed into a good silage or whether the ensiling process requires the addition of further substances to improve fermentation of harvested crops.

BRIEF DESCRIPTION OF THE INVENTION

According to a first aspect, the invention is directed to a method of preparing of a silage good having improved quality to be subjected to an ensiling process, the method comprising;
  subjecting a freshly harvested good to be subjected to the ensiling process to an analysing process for determining a plurality of parameters $x_i$ characterising a chemical composition and/or a property of the harvested good;
  applying a first model on the determined parameters $x_i$ to determine an ensilability index number Ini, that is characteristic for an expected ensilability of the harvested good;
  applying a second model on the determined parameters $x_i$ to determine a retention index number Rei, that is characteristic for an expected loss of dry matter of the harvested good during the ensiling process;
  determining types and amounts of ensiling additives to be added to the harvested good for controlling the ensiling process depending on the ensilability index number Ini and the retention index number Rei; and
  supplying the determined additives to the harvested good to obtain the silage good, in case the determined amount of the ensiling additive exceeds zero.

In contrast to the prior art which assesses the quality of the silage product, the method of the invention determines the potential of harvested good to be transformed into a good silage product, thereby allowing to anticipate the capability of undergoing a favourable fermentation process as well as the risk of losing dry matter during the ensiling process. Furthermore, the method of the invention enables the farmer to optimize the ensiling process by selecting appropriate ensiling additives to be added in order to influence the ensiling process. This is not possible with the already known quality index scores such as the Flieg-Zimmer's score or others, which describe the quality of corn silage after the fermentation process, so that no fine-tuning of the ensiling process is possible to obtain an improved silage product.

The method of the invention thus employs two indices, namely:
  (1) the ensilability index number, also referred to as Ini, and
  (2) the retention index number, also referred to as Rei.

The ensilability index number Ini is indicative for an expected ensilability of the harvested good. It thus represents the relationship between the chemical composition of the freshly harvested good (expressed by parameters $x_i$) and the quality of the silage product, i.e. its chemical composition. The latter may be expressed by a quality index score known in the art, such as the Flieg-Zimmer's score (FZS), the German agricultural society's (DLG) and Vanbelle's scores, or one of the quality indexes I1-I6 as previously described by Andrighetto et al. (Andighetto et al., supra). The ensilability index number therefore correlates the chemical composition of the harvested good with the theoretical maximum value of the quality index which can be obtained from the harvested good after transformation into a silage product.

The retention index number Rei, on the other hand, is indicative for an expected loss of dry matter (or the expected retention of dry matter) during the ensiling process. It thus represents the relationship between the chemical composition of the freshly harvested good (expressed by parameters $x_i$) and the dry matter content of the silage product.

Accordingly, the method according to the present invention considers both, the expected quality of the chemical composition and the expected dry matter content of the silage good obtained by the ensiling process, in order to allow the farmer to positively influence the ensiling process, if necessary.

For the purpose of the present description, the term "harvested good" or "freshly harvested good" refers to a crop after the harvest without being subjected to any modification, including addition of substances or modification by processes influencing the chemical composition. The term "silage good" refers to the good to be subjected to an ensiling process, i.e. the good before ensiling. Thus, the silage good is the sum of the harvested good and any silage additive supplied to the harvested good. In case no additive is added, the silage good and the harvested good are identical. This means that the harvested good is the silage good, if the herein described indexes indicate that the harvested good can be converted into a good silage product without the supply of silage additives. If, however, the herein described indexes indicate that the harvested good cannot be converted into a good silage product, then additives are supplied to the harvested good. In the latter case, the silage good is then the sum of the harvested good and any additive supplied to it. Further, the term "silage product" refers to the product of the ensiling process, in particular the product of microbiological fermentation. The silage product is the result of microbiological fermentation of the silage good, i.e. the harvested good and any silage additive supplied to it if necessary.

The expression "loss of dry matter" in the context of the present invention is to be understood as the mass or the variation of mass [%] between the harvested/silage good and the silage product. It should not be merely understood as the composition or variation in chemical composition [%]. For example, 10 kg of fresh sample (before ensiling) at 30% of dry matter content means 3 Kg of mass of dry matter. In the same example, the sample after ensiling weight 9 Kg (1 Kg is lost because of liquid leach, sugar consumption, gas etc.) but in term of chemical composition has 31% of dry matter content, which corresponds to a mass of 2.79 Kg of dry matter. Thus, chemical composition of dry matter content increase from 30% to 31%, but in term of dry matter mass it decreases from 3 Kg to 2.79 Kg, and the loss in term of dry matter mass percentage is 7%.

Further for the purpose of the present description, the expression "silage good having improved quality" refers to a silage good that has a higher content of favourable nutrient components and/or a higher content of dry matter after having been subjected to an ensiling process compared to a silage good not having been modified by addition of silage additives according to the invention, when subjected to an ensiling process using the same conditions.

The harvested good may be any crop which is capable of being processed by ensiling, i.e. by fermentation processes. The harvested good may for instance be selected from corn, such as maize (*Zea mays*), sorghum, such as *Sorghum bicolor* and sudanese, sugar cane, such as *Saccharum officinarum*, rye, such as *Secale cereale* L., barley, such as *Hordeum vulgare*, wheat, such as *Triticum aestivum L.*, triticale, lolium, such as *Lolium perenne*, alfalfa, such as *Medicago sativa*, and others. From these, maize is of particular interest as maize silage is one of the most widely used feed in cattle rations in great parts of the world since it is a very productive crop, characterized by an excellent nutritional profile and high susceptibility of being preserved through ensiling.

The analysing process for determining the parameters $x_i$ may apply any method capable of providing information on the chemical composition and/or another property of the harvested good. In preferred embodiments, the analysing process may include a spectroscopic method, such as infrared spectroscopy (preferably near infrared spectroscopy), terahertz spectroscopy (preferably teraherz time-domain spectroscopy), Raman spectroscopy, ultraviolet spectroscopy, mass spectroscopy, such as MALDI-TOF spectroscopy, nuclear magnetic spectroscopy, laser induced breakdown spectroscopy or others. Alternatively, the analysing process may include chromatographic methods, such as gas chromatography (GC), high-performance liquid chromatography (HPLC) or others. In still other examples the analysing process may include thermal imaging methods, wet analysis, and elemental trace analysis. One or more methods of each category may be combined to enhance the quantity of information assessed from the harvested good. Preferred methods include those which are quick, robust and capable of being conducted in-line on field conditions. Here, spectroscopic methods have proven to be particularly useful, preferably infrared spectroscopy, and most preferably near infrared spectroscopy (NIR), since NIR allows determining a high number of parameters of interest in one measurement The parameters $x_i$ determined in the analysing process step may comprise any ingredient present in the harvested good, in particular those which are known to undergo or to influence (favourable or undesired) fermentation processes during ensiling. Accordingly, preferred parameters may be selected from a content of water, dry matter (DM), ash (A), acid insoluble ash (AIA), crude protein (CP), total sugar (TS), glucose (GLU), fructose (FRU), saccharose (SAC), total ether extract (EE), starch, cellulose, hemicellulose, lignin, crude fibre (CF), acid detergent fibre (ADF), neutral detergent fibre (NDF), and acid detergent lignin (ADL). Moreover, parameters characterising other properties of the harvested good, such as the pH value may be determined. However, the parameters applicable in the present method are not limited to those mentioned above.

The number of parameters $x_i$ determined in the analysing process step is not particularly limited as long as the number is appropriate to derive the ensilability index number and the retention index number. For instance, the number of parameters $x_i$ determined in the analysing process step may range between 2 and 20, preferably 3 to 15, and even more preferred 4 to 10. The higher the number of the determined parameters $x_i$ the more predictive will be the index numbers Ini and Rei. On the other hand, the complexity of the method increases with the number, so that the number will usually be a compromise between reliability and complexity.

The first model allows deriving the ensilability index number Ini as a function of the parameters $x_i$. The first model may be a mathematical function, a look-up table or the like, stored in a computer-readable format.

According to a preferred embodiment of the invention, the first model applied in the method in order to determine the ensilability index number Ini is obtained by correlating parameters $x_{i,e}$ which have been measured from test samples before ensiling with the chemical composition of the silage product obtained after ensiling at predetermined conditions. In other words, the first model may be obtained empirically by experiments involving (a) collecting test samples of a freshly harvested good, (b) determining parameters $x_{i,e}$ of the test samples corresponding to the parameters $x_i$ determined in the analysing process step, (c) subjecting the test samples to an ensiling process at predetermined conditions, (d) determining the chemical compositions of the silage products of the test samples, and (e) correlating the chemical compositions of the silage products with the parameters $x_{i,e}$ of the test sample before ensiling thus deriving the first model. Preferably, the correlation step (e) comprises assigning a quality index to the silage product according to its chemical composition, such as the Flieg-Zimmer's score (FZS), the German agricultural society's (DLG) and Vanbelle's scores, or one of the quality indices I1-I6 of Igino Andrighetto et al. (see above), and correlating the quality index with the parameters $x_{i,e}$ of the test samples. The correlation step may involve a mathematical regression analysis resulting in a mathematical function (including regression parameters) expressing the ensilability index number Ini as a function of the parameters $x_i$.

The second model allows deriving the retention index number Rei as a function of the parameters $x_i$. The second model may be a mathematical function, a look-up table or the like, stored in a computer-readable format.

According to a preferred embodiment of the invention, the second model applied in the method in order to determine the retention index number is obtained by correlating parameters $x_{i,e}$ which have been measured from test samples before ensiling with the dry matter content of the obtained silage product after the ensiling at predetermined conditions. In other words, the second model may be obtained empirically by experiments involving (a) collecting test samples of a freshly harvested good, (b) determining parameters $x_{i,e}$ of the test samples corresponding to the parameters $x_i$ determined in the analysing process step, (c) subjecting the test samples to an ensiling process at predetermined conditions, (d) determining the dry matter content of the silage products of the test samples, and (e) correlating the dry matter contents of the silage products with the parameters $x_{i,e}$ of the test sample before ensiling thus deriving the second model. The correlation step may involve a mathematical regression analysis resulting in a mathematical function (including regression parameters) expressing the index number Rei as a function of the parameters $x_i$.

Typically, ensilability index number Ini and the retention index number Rei will independently be a dimensionless number or a percentage.

According to a preferred embodiment of the invention, the step of determining types and amounts of ensiling additives to be added to the harvested good comprises:
  comparing the ensilability index number Ini to a first threshold value and depending on whether the determined ensilability index number exceeds or falls below the first threshold value, the type and content of an additive selected from a first group of additives is determined; and
  comparing the retention index number Rei to a second threshold value and depending on whether the determined ensilability index number exceeds or falls below the first threshold value, the type and content of an additive selected from a second group of additives is determined.

According to one embodiment of the invention, additives from the first and second group of additives are selected from homofermentative and/or heterofermentative organisms, more preferably from *Lactobacillus plantarum, Lactobacillus casei, Lactobacillus delbruckii* subs. *bulgaricus*, Lb. *acidophilus*, Lb. *helveticus, Streptococcum faecium, Streptococcus salivarius* subsp. *thermophilus; Streptococcus* spp., *Pediococcus pentosaceus, Lactobacillus curbatus, Lactobacillus coryniformis* subs. *coryniformis*, and *Pediococcus acidilactici, Enterococcus, Pediococcus* and *Aerococcus, Lactobacillus brevis, Lactobacillus buchneri, Lactobacillus fermentum, Lactobacillus reuteri, Lactobacillus viridescens, Lactobacillus rhamnosus, Leuconstoc cremoris* (*Leuconostoc mesenteroides* ssp. *cremoris*), *Lactobacillus platarum, Lactobacillus casei, Lactobacillus curvatus* and *Leuconstoc dextranicum*. Other additives of the first group may comprise one/or more sugars, such as glucose, fructose, sucrose, and derivatives thereof, one or more acidifying compound, such as formic acid, propionic acid, lactic acid, and/or water. Combinations of the aforementioned additives may be applied as well.

In a preferred embodiment of the invention, the first group of additives may be applied to harvested good having a poor ensilability index number. According to the preferred embodiment, the first group of additives preferably comprises homofermentative microorganisms. For instance, the first group of additives may be selected from inoculates of different bacterial strains, such as *Lactobacillus plantarum, Lactobacilum casei, Lactobacillus delbruckii* subs. *bulgaricus*, Lb. *acidophilus*, Lb. *helveticus, Streptococcusecium, Streptococcus salivarius* subsp. *thermophilus; Streptococcum* spp., *Pediococcus pentosaceus, Lactobaciluss curbatus, Lactobaciluss coryniformis* subs. *coryniformis*, and *Pediococcus acidilactici, Enterococcus, Pediococcus* and *Aerococcus*. Other additives of the first group may comprise one/or more sugars, such as glucose, fructose, sucrose, and derivatives thereof, one or more acidifying compound, such as formic acid, propionic acid, lactic acid, and/or water. Combinations of the aforementioned additives may be applied as well. The term "homofermentative microorganisms" as used herein refer to lactic acid bacteria which ferment glucose with lactic acid as the primary by-product. Homofermentative microorganisms are used in fermentation processes where the rapid development of lactic acid and reduced pH is desirable.

According to a further preferred embodiment, the second group of additives may be applied to harvested good having a poor retention index number, i.e. which are expected to undergo a high loss of dry matter during fermentation. According to the further preferred embodiment, the second group of additives preferably comprises heterofermentative microorganisms. For instance, the second group of additives may be selected from inoculates of different bacterial strains, such as *Lactobacillus brevis, Lactobacillus buchneri, Lactobacillus fermentum, Lactobacillus reuteri, Lactobacillus viridescens, Lactobacillus rhamnosus, Leuconstoc cremoris* (*Leuconostoc mesenteroides* ssp. *cremoris*), *Lactobacillus platarum, Lactobacillus casei, Lactobacillus curvatus* and *Leuconstoc dextranicum*. Other additives of the second group may comprise one or more sugars, such as glucose, fructose, sucrose and derivates thereof, one or more acidifying compound, such as formic acid, propionic acid, lactic acid, and/or water. Combinations of the aforementioned additives may be applied as well. The term "heterofermentative microorganisms" as used herein refer to lactic acid bacteria which ferment glucose with lactic acid, ethanol/acetic acid and carbon dioxide ($CO_2$) as by products. Heterofermentative microorganisms are used in fermentation processes.

In case a harvested good is found to have both, a poor ensilability index number and a poor retention index, additives of the first and the second groups may be applied to the harvested good. Moreover, in case the harvested good is found to have both, a favourable ensilability index number and a favourable retention index, no additives will be applied.

It is particularly preferred that the method is carried out in a continuous manner during harvesting the harvest good, i.e.

at field-conditions. In other words, according to this embodiment the determination of the ensilability index number and retention index as well as the addition of the additives is conducted on the field as an in-line process with the harvest, so that the silage good is obtained on the field and can be directly provided to the ensiling process.

Another aspect of the present invention is directed to an ensiling process comprising:
preparing a silage good by the method according to the first aspect as described herein; and
subjecting the silage good to fermentation to obtain a silage product.

Yet another aspect of the present invention is directed to an apparatus for preparing a silage good having improved quality to be subjected to an ensiling process, the apparatus comprising:
analysing means for analyzing a freshly harvested good for determining a plurality of parameters $x_i$ characterising a chemical composition and/or a property of the harvested good;
a first model correlating the determined parameters $x_i$ with an ensilability index number Ini, that is characteristic for an expected ensilability of the harvested good;
a second model correlating the determined parameters $x_i$ with a retention index number Rei, that is characteristic for an expected loss of dry matter of the harvested good during the ensiling process;
determination means for determining types and amounts of ensiling additives to be added to the harvested good for controlling the ensiling process depending on the ensilability index number Ini and the retention index number Rei; and
supply means for adding the determined additives to the harvested good to obtain the silage good, in case the determined amount of the ensiling additive exceeds zero.

The analysis means comprise devices suitable for performing the determination of the parameters. In preferred embodiments, the analysing means may include a spectrometer, such as infrared spectrometer (preferably near infrared spectrometer), terahertz spectroscopy (preferably terahertz time-domain spectroscopy), Raman spectrometer, ultraviolet spectrometer, mass spectrometer, such as MALDI-TOF spectrometer, nuclear magnetic spectroscopy, laser induced breakdown spectrometer or others. Alternatively, the analysis means may include at least one chromatograph, such as a gas chromatograph (GC), a high-performance liquid chromatograph (HPLC) or others. In still other examples the analysing means may include a thermal imaging device, a wet analysis device, and/or an elemental trace analysis device. One or more devices of each category may be combined to enhance the quantity of information assessed from the harvested good. Preferred analysis means include those which enable quick and robust measurements and are capable of being used in-line on field conditions. Here, spectrometers have proven to be particularly useful, preferably infrared spectrometers, and most preferably near infrared spectrometers.

The apparatus may further comprise a device for heading, chopping, threshing, crushing, mashing, grinding or peeling the harvested good, for instance a field chopper for chopping the harvested good. Here it is particularly preferred that the device is equipped with the analysing means to enable conducting the analysis on the field, for instance the field chopper is equipped with the analysing means.

The apparatus may further comprise a conveying mean, such as a convey belt or the like, for transporting the harvested good, optionally processed by means of the above device for heading, chopping, threshing, crushing, mashing, grinding or peeling, from the harvesting means to the analysing means and/or from the analysing means to the supply means and from the supply means to an ensiling tank.

The apparatus may further comprise an equalizing mean for homogenizing or evenly distributing the harvested good, optionally processed by means of the above device for heading, chopping, threshing, crushing, mashing, grinding or peeling, for generating a uniform stream of the (processed) harvested good. Such equalizing mean allows an improved or optimized presentation of the harvested good to the analysing means, for example by smoothing the surface of the stream of (processed) harvested good. One example for such equalizing mean is a roller in the form of an elongate shaft, which preferably is arranged at a constant and fixed distance along the roll axis above the conveyer belt directing the (processed) harvested good to the analyzing means. Using this roller, the (processed) harvested good can be compressed to a certain thickness, whereby a smooth surface results. Preferably, a motor drives the roller and rotates it in the running direction of conveyer belt, more preferably the movement of the roller is coupled with drive of the conveyer belt. Below the belt, a block or another roller can be provided, for providing a counterpart for the pressure of the first roller. Block or another ensure that the belt is not pushed downwards and thus, the stream of (processed) harvested good substantially has a preselected height after passing the first roller. In a second example, for irradiation-based analyzing means, preferably infrared spectroscopy, more preferably near infrared spectroscopy, the stream of (processed) harvested good is passed or directed along a window for transferring respective irradiation between analysing mean and (processed) harvested good. The window material, such as glass or Perspex, can be removed for cleaning or replacement. Cleaning or replacement of the window material may be necessary as debris from the processing stream such as processed harvested good passing the window can build up on the window material or damage the window material, interfering with operation of the system. By passing the (processed) harvested good along the window, the stream and the surface of the stream on the side of the window is equalized.

Further embodiments of the present invention are defined in the depending claims and present description. All embodiments may be combined with each other, if not indicated otherwise.

BRIEF DESCRIPTION OF THE FIGURES

The invention will now be described in more detail in terms of preferred embodiments referring to the figures showing.

DETAILED DESCRIPTION OF THE INVENTION

Figure 1:
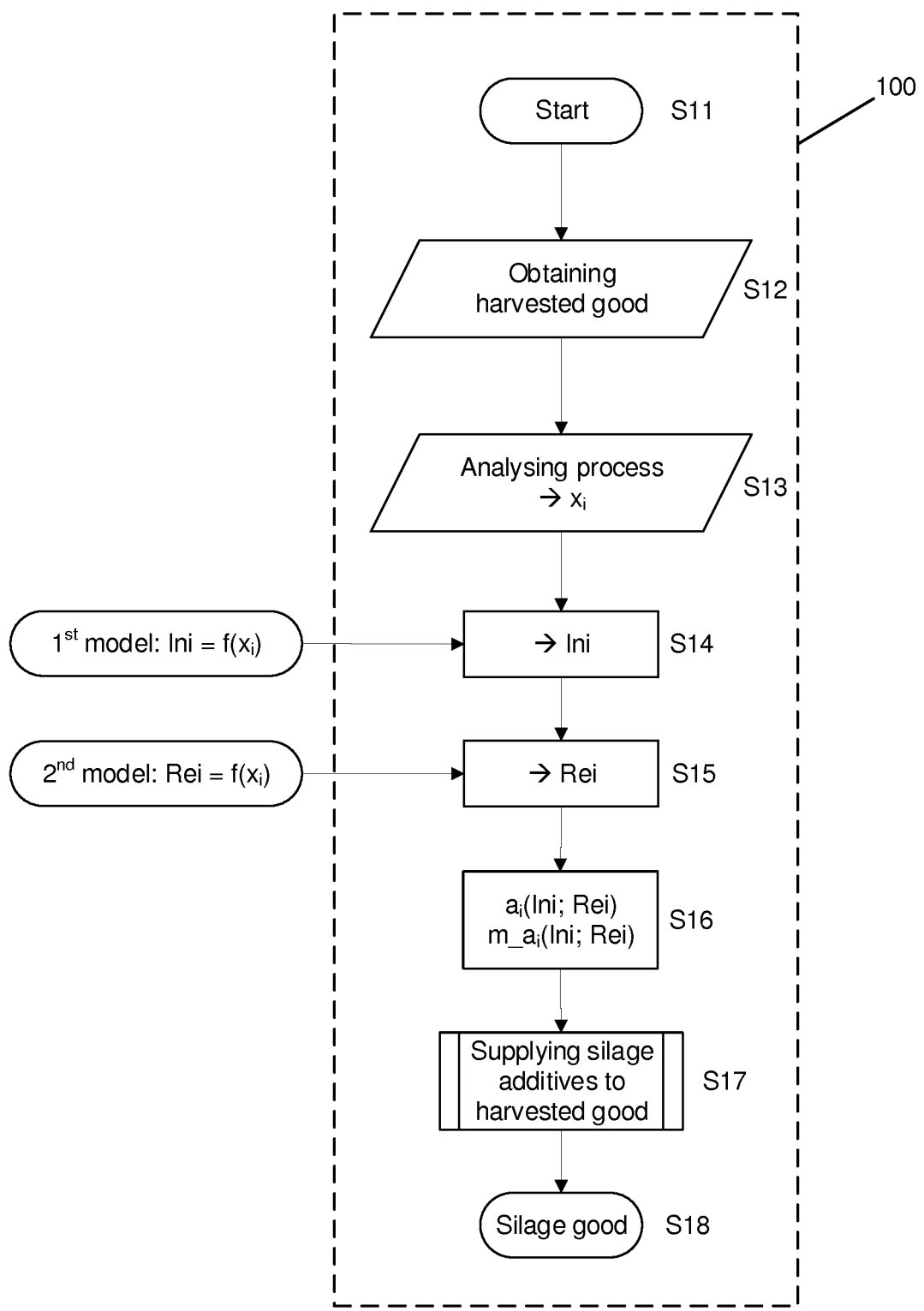
FIG. 1 flow chart of a method of preparing of a silage good according to a preferred embodiment of the invention.

FIG. 1 shows a flow chart of a method 100 of preparing of a silage good according to a preferred embodiment of the invention.

The method starts in step S11 and proceeds to step S12, where a harvested good is obtained. This step includes commonly known agricultural harvesting processes. Harvesting may be conducted manually, but will usually be performed using agricultural harvesting machines. In addition to the harvesting, process step S12 may optionally include mechanically processing the harvested good, such as heading, chopping, threshing, crushing, mashing, grinding or peeling in order to transform the harvested good to a size or shape suitable for ensiling and/or equalizing/homogenizing the (processed) harvested good. The harvested good may comprise any agricultural crop suitable to be subjected to ensiling, particularly those mentioned before, for instance maize. In case of maize, the harvested good is the entire above-ground plant or just the maize grains.

In the next step S13, the harvested and optionally mechanically processed/equalized good is subjected to an analysing process for determining a plurality of parameters $x_i$ characterising a chemical composition and/or another property/characteristic of the harvested good. Here x denotes the parameter obtained by the analysis and the index i denotes an index number running from 2 to N, where N means the total number of parameters determined in the method. The parameter may include any component included in the harvested good, particularly those mentioned before. According to a particular example, in step S13 seven parameters $x_i$ may be determined, comprising the dry matter content (DM), the total sugar content (TS), the total lipid content (EE), the acid detergent fibre content (ADF), the acid detergent lignin content (ADL), the neutral detergent fibre content (NDF), and the starch content (ST). The analysing process for determining the parameters $x_i$ may apply any method capable of providing the information of interest, particularly those mentioned before. According to a particularly preferred example, in step S13 near infrared (NIR) spectroscopy is employed as it is capable of determining all of the mentioned parameters.

Next, the procedure proceeds to step S14, where a first model $Ini=f(x_i)$ is applied on the parameters $x_i$ determined in step S13 in order to determine the ensilability index number Ini that is characteristic for an expected ensilability of the harvested good. The ensilability index number Ini indicating the expected quality of the silage product after ensiling and may be a dimensionless number. Preferably, the ensilability index number Ini represents a score ranging between a worst quality of the silage product and a theoretical maximum quality. The first model may be stored in form of a multi-dimensional look-up table assigning the ensilability index number Ini to the parameters $x_i$. Alternatively, the first model may be a mathematical equation expressing the ensilability index number Ini as a function of the parameters $x_i$. An example, for a mathematical equation obtained by regression analysis representing the first model is shown in Eq. 1 below:

$$Ini = \text{Intercept} + \sum_{i=1}^{N} C_i x_i + \sum_{i=1}^{N} B_i x_i^2$$

Here, $C_i$ and $B_i$ represent the first order and second order regression coefficients for the $i^{th}$ parameter x, respectively. The first model is obtained beforehand involving empirical studies. An example for obtaining the first model will be described below by means of FIG. 2. The result of step S14 is thus the ensilability index number Ini in form of a single characteristic value.

Next, the procedure proceeds to step S15, where a second model $Rei=f(x_i)$ is applied on the parameters $x_i$ determined in step S13 in order to determine the retention index number Rei that is characteristic for an expected loss or retention of dry matter of the harvested good during the ensiling process. The retention index number Rei may be a dimensionless number or a percentage. It thus represents the relationship between the chemical composition of the freshly harvested good (expressed by parameters $x_i$) and the expected dry matter of the silage product. For instance, the retention index number Rei represents a score ranging between a theoretical minimum loss of dry matter and a theoretical maximum loss of dry matter during ensiling. Likewise the first model, the second model may be stored in form of a multi-dimensional look-up table assigning the retention index number Rei to the parameters $x_i$. Alternatively, the second model may be a mathematical equation expressing the retention index number Rei as a function of the parameters $x_i$. An example, for a mathematical equation obtained by regression analysis representing the second model is shown in Eq. 2 below:

$$Rei = \text{Intercept} + \sum_{i=1}^{N} D_i x_i + \sum_{i=1}^{N} E_i x_i^2$$

Here, $D_i$ and $E_i$ represent the first order and second order regression coefficients for the $i^{th}$ parameter x, respectively. The second model is obtained beforehand involving empirical studies. An example for obtaining the second model will be described below be means of FIG. 3. The result of step S15 is thus the retention index number Rei in form of a single characteristic value.

After having determined the ensilability index number Ini and the retention index number Rei, the method proceed to step S16, where a type $a_i$ of ensiling additive(s) and the amount m_ai of the respective additive to be added to the harvested good for controlling the ensiling process are determined on basis of the ensilability index number Ini and the retention index number Rei.

Step S16 may involve a look-up table assigning type and amount of the ensiling additive to Ini and Rei. Alternatively, Step S16 may involve a mathematical function expressing type $a_i$ and amount m_ai of additive as a function of to Ini and Rei. According to a specific embodiment, in step S16 a decision may be made whether or not the ensilability index number Ini exceeds a first threshold value $Ini_1$. Depending on whether Ini exceeds or falls below the first threshold value $Ini_1$, the type and content of an additive selected from a first group of additives mentioned above is determined. As the ensilability index number Ini indicates the susceptibility of the chemical ingredients of the harvested good to be transformed into a high-quality silage product, the first group of additives preferably comprise homofermentative microorganisms, sugars and/or water, in particular those mentioned before. Likewise, in step S16 a decision may be made whether or not the retention index number Rei exceeds a second threshold value $Rei_1$. Depending on whether Rei exceeds or falls below the second threshold value $Rei_1$, the type and content of an additive selected from a second group of additives mentioned above is determined. As the retention index number Rei indicates the expected dry matter loss during the ensiling process, the second group of additives preferably comprise heterofermentative microorganisms, in particular those mentioned before. It is understood that, in case that the indices Ini and Rei indicate that the harvested good is expected to be easily transformed into a high-quality silage product at low loss of dry matter, there may be no need to add any additive to the harvested good. In this case, the amounts of additives to be added are determined to be as low as zero.

Figure 4:
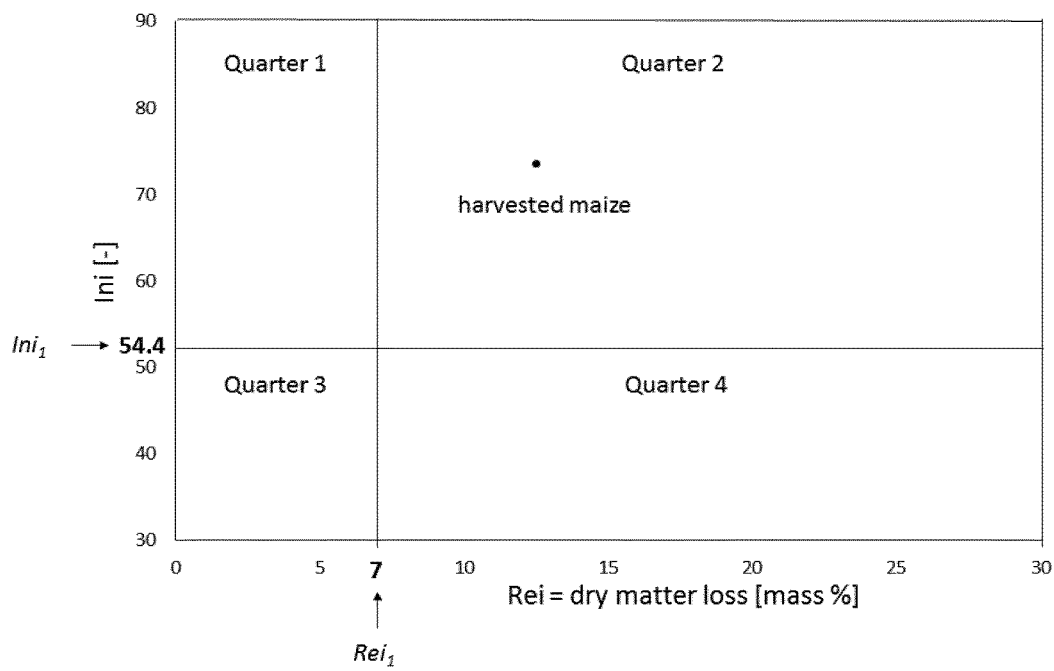
FIG. 4 graphical representation of the ensilability index number and retention index number of a harvested good determined by the method of the invention.

For the purpose of step S16, the determined ensilability and retention indices Ini and Rei may be visualized in a two-dimensional graphical representation as shown in FIG. 4 (harvested good=maize). Here, the retention index number Rei is shown on the x-axis in form of the percentage of dry matter loss (based on the total dry matter of the harvested good), and the ensilability index number Ini is depicted on the y-axis. The first threshold value $Ini_1$ for the ensilability index number corresponds in this example to a value of 54.4, whereas the second threshold value Rei corresponds to a dry matter loss of 7 mass %. By way of these thresholds the field is divided in four quarters (quarter 1 to quarter 4). In this, way the harvested good is assigned to one of quarters 1 to 4 (for instance quarter 2 as indicated in FIG. 4), leading to one of the following scenarios:

Quarter 1 (Ini>54.4; Rei<7%): the maize has balanced chemical composition allowing rapid activation of positive fermentation process. No ensiling additives correction required for stimulation of fermentation.

Quarter 2 (Ini>54.4; but Rei>7%): maize has good chemical composition but not able to effectively contain conservation losses (possibly because of high content of moisture of the freshly chopped maize). Use additives (heterofermentative and/or homofermentative microorganisms) to accelerate and optimize the fermentation process.

Quarter 3 (Rei<7%; but Ini<54.4): chemical composition not able to effectively stimulate fermentation. If dry matter content is higher than 45% it is necessary to use additives (heterofermentative and/or homofermentative microorganisms, water and sugar) to obtain sufficient fermentation.

Quarter 4 (Ini<54.4; Rei>7%): good chemical composition but established process not ideal for the quality and retention of dry matter, i.e. the chemical composition does not demonstrate good suitability for fermentation due to inadequate ratio spike/stover, and the fermentation processes are not ideal for the quality and retention of dry matter. Add additives to improve fermentation process.

Again referring to FIG. 1, after having determined the types $a_i$ and amounts $m\_a_i$ of ensiling additives, the procedure proceeds to step S17, where the additives determined in step S16 are supplied to the harvested good at the corresponding amounts. Supply of additives can be performed by any suitable method depending on the form of the additive. Preferably, the additives are supplied in form of solutions or suspensions by spraying or the like. In this way, a homogeneous distribution or mixture of the additive(s) in the harvested good is obtained.

The method ends in step S18 with obtaining the silage good, including the harvested good plus additive(s), which is ready to be subjected to ensiling.

According to a preferred embodiment, the method 100 is continuously conducted as an in-line process during the harvest. In this way, the parameters $x_i$ may be determined continuously in a step-by-step manner for fresh cut fractions of the harvested good. This enables to continuously supply the additives to the respective crop fractions depending on the composition of the respective fraction and to prepare different fractions of the silage good differing in the kind and/or amount of supplied additive. The various fractions of the silage good can thus be supplied to an ensiling tank.

Next, the methods of obtaining the first and second models used in the method in FIG. 1 will be described in FIGS. 2 and 3, respectively. It is assumed that these models are obtained only once to be continuously used in the method of FIG. 1.

Figure 2:
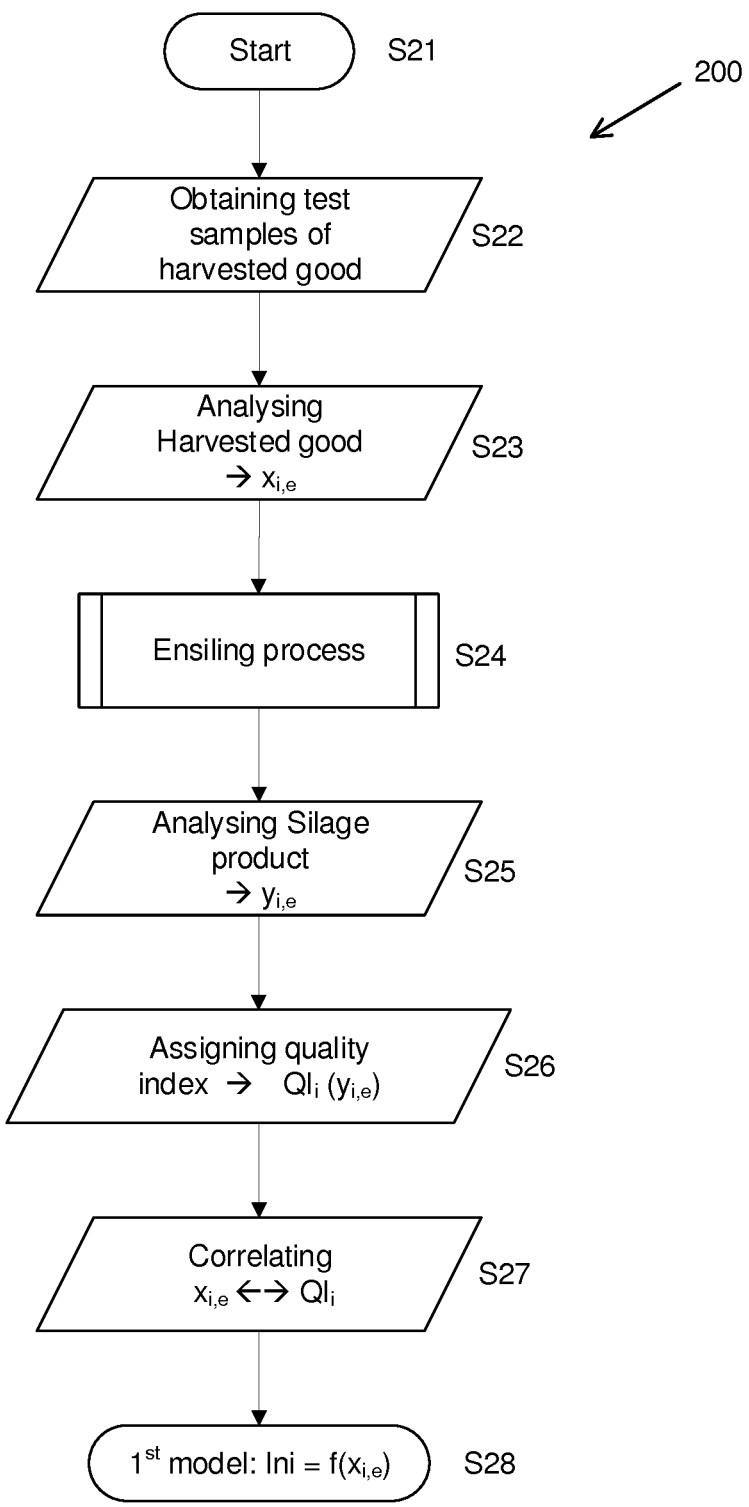
FIG. 2 flow chart of a method of obtaining the first model to determine the ensilability index number used in the method of FIG. 1.

Referring to FIG. 2 the method 200 of obtaining the first model for determining the ensilability index number Ini as a function of parameters $x_i$ is described.

The method starts in step S21 and proceeds to step S22, where test samples of harvested goods of a crop of interest are collected. Preferably, the samples are collected from different cultivars, different climatic conditions, and different harvest periods in order to provide a broad distribution of compositions. In a particular example, test samples of maize have been collected from 29 cultivars (including early and late cultivars), three sites of production (different for pedological and climatic conditions) and in anticipate or normal or posticipate harvest period. All test samples have been chopped after harvest.

The process then proceeds to step S23, where the test samples are analysed for determining experimental parameters $x_{i,e}$ characterising a chemical composition and/or a property of the harvested test samples. Here, the experimental parameters $x_{i,e}$ and the analysing methods may be the same as described for step S13 in FIG. 1.

The process then proceeds to step S24, where the test samples are transformed to a silage product by an ensiling process using predetermined standard conditions. Preferably the predetermined conditions are favourable conditions, where optimized or optimal fermentation is expected. The ensiling process may be conducted in large-scale silos at field conditions or at lab-scale conditions. In the particular example, the ensiling process was conducted at the following lab-scale conditions: Two samples (500±50 g) for each freshly harvested whole maize chopped crop were placed in vacuum-packed bags (Orved 2633040, Orved SpA, Musile di Piave, VE, Italy). Bags (300×400 mm) of 90 μm thick, were made of polyamide and polyethylene (PA/PE) with gas permeability at 23° C.±2 of 65, 15 and 200 $cm^3$ $m^{-2}$ $day^{-1}$ $atm^{-1}$ to oxygen, nitrogen and $CO_2$, respectively. Vacuum-packing was performed using a vacuum-packing machine (Cuisson 41, Orved SpA, Musile di Piave, VE, Italy) drawing 25 $m^3$ of air per hour for 12 s. Bags were then automatically sealed after air extraction. Samples were treated to avoid bloating and stored at 23° C. for 60 days, before being opened for analysis.

In step S25 the silage product of the test samples is again subjected to an analysis process in order to determine second experimental parameters $y_{i,e}$ that are characteristic for the chemical composition and/or other properties of the silage product. The parameters determined here may be selected from the pH value, lactic acid content, acetic acid content, butyric acid content ethanol content, mannitol content, ammonia content. In addition, the same parameters mentioned with respect to parameters $x_i$ before may be determined in step S25. Further, the same analysing methods described before may be applied in this step. In the particular example, the content of each of the bags was analysed in duplicate by NIR-spectroscopy in order to determine the content of dry matter (DM), crude protein (CP), ash (AS), starch (STA), ether extract (EE), neutral detergent fibres (NDF), and acid detergent fibre (ADF) using a calibration curve. The contents of lactate, volatile fatty acids (VFA), ethanol and mannitol were determined by HPLC. Ammonia was measured using an assay kit (Megazyme). Further, the pH was measured. Average values are then calculated for each parameter.

In subsequent step S26 a quality index Q/is assigned to each silage test sample depending on the parameters $y_{i,e}$. Here a quality index Q/known in the art for assessing the quality of silage products may be applied. In the particular example, one of the quality indices I1 to I6 described by Igino Andrighetto et al. (Andrighetto et al., supra) have been applied. As shown in Table 1, indices I1 to I6 are based on the contents of lactic acid, ammonia, ethanol, acetic acid, butyric acid, mannitol and the pH value. For each parameter $y_{i,e}$ a score interval was predetermined correlating with the range of content values (based on dry matter DM). For example, the minimum content of lactic acid (22.6 g/kg DM) will be scored with 0 and the maximum content of lactic acid (60.0 g/kg DM) will be scored with 41, etc. The maximum quality index is 100 for each of the indices I1 to I6.

TABLE 1

| Parameters $y_{i,e}$ | Range of values (g/kg DM) | Score interval | | | | | |
|---|---|---|---|---|---|---|---|
| | | I1 | I2 | I3 | I4 | I5 | I6 |
| Dry matter (g/kg) | 390-276 | — | — | — | — | — | 0-6 |
| NDF | 518-410 | — | — | — | — | — | 0-39 |
| ADF | 297-220 | — | — | — | — | — | 0-2 |
| Lactic acid | 22.6-60.0 | 0-41 | 0-41 | 0-41 | 0-41 | 0-41 | 0-17 |
| Ammonia | 82.0-35.4 | 0-18 | 0-18 | 0-18 | 0-18 | 0-18 | — |
| Ethanol | 8.70-2.10 | 0-18 | 0-18 | 0-18 | 0-18 | 0-18 | — |
| Acetic acid | 27.4-7.20 | 0-9 | 0-9 | 0-9 | 0-9 | 0-9 | 0-20 |
| pH [a] | 3.97-3.65 | 0-8 | 0-4 | 0-4 | 0-6 | — | — |
| Butyric acid | 1.00-0.00 | — | 0-10 | 0-7 | 0-2 | 0-14 | — |
| Mannitol | 12.7-0.90 | 0-6 | — | 0-3 | 0-6 | — | 0-16 |
| Index maximum score | — | 100 | 100 | 100 | 100 | 100 | 100 |

[a] It is expressed as a pure number.

Accordingly, in step S26, a quality index $QI_i$ is obtained for each silage product depending on its chemical composition.

Then the method proceeds to step S27, where the quality indices $QI_i$ are correlated with the parameters $x_{i,e}$ determined in step S23 before ensiling. The correlation step may involve a mathematical regression analysis resulting in a mathematical function (including regression parameters) expressing the ensilability index number Ini as a function of the parameters $x_{i,e}$. In the present example, the inventors have used the data from all analysed maize plants without or after transformation (logarithmic, squared, etc.) or combinations of them. Also, many regressions have been calculated using software named SAS, differing in the considered parameters (analysis) and/or the applied transformation. At the end, a regression with the higher R-square value has been adopted yielding the best correlation (cf. Eq. 1 above). Table 2 shows the regression parameters of the regression function obtained for the maize test samples.

TABLE 2

Regression coefficients of the first model for predicting the ensilability (values are calculated on % of Dry Matter basis)

| Parameters $x_{i,e}$ | Intercept 197.11574 | $C_i$ | $B_i$ |
|---|---|---|---|
| Dry matter (DM) | | −6.83667 | 0.07552 |
| Total Sugars (TS) | | 0.27189 | 0 |
| Lipids (EE) | | 11.37159 | 0 |
| ADF | | 1.68108 | 0 |
| ADL | | 12.55362 | 0 |
| NDF | | 0 | −0.01528 |
| Starch (STA) | | 0 | −0.00939 |

The regression function $Ini=f(x_{i,e})$ according to the first model using the regression coefficients of Table 2 can be thus be expressed as follows (Eq. 1.1):

$$Ini=197.11574-6.83667DM+0.27189TS+11.37159EE+1.6810ADF-12.55362ADL+0.07552DM^2-0.01528NDF^2-0.00939STA^2$$

The procedure of FIG. 2 thus ends in step S28 thus providing the first model $Ini=f(x_{i,e})$ which can then be applied in the procedure of FIG. 1 for determining the expected ensilability of the new harvested maize.

Figure 3:
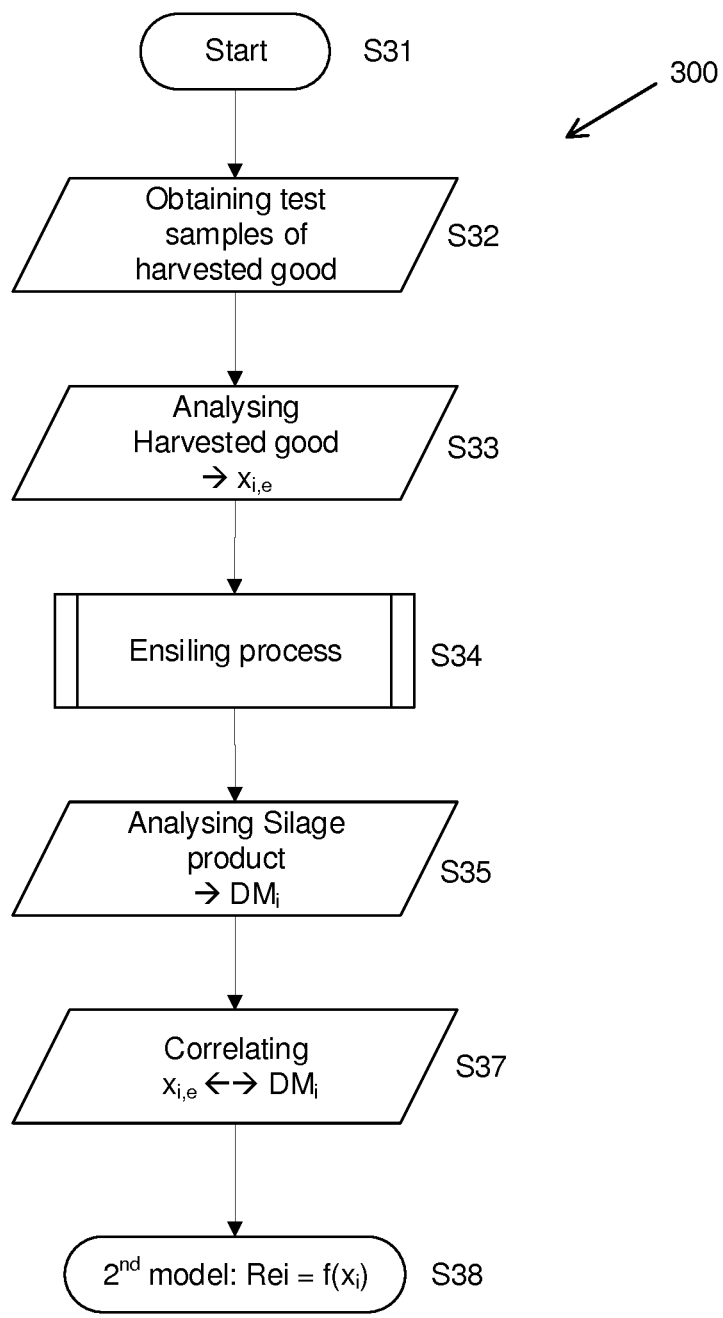
FIG. 3 flow chart of a method of obtaining the second model to determine the retention index number used in the method of FIG. 1.

Referring to FIG. 3, the method 300 of obtaining the second model for determining the retention index number Rei as a function of parameters $x_i$ is described.

Here, steps S31 to S34 correspond to steps S21 to S24 of FIG. 2 and are not explained again. In fact, both of the methods for determining the first model for the ensilability index and for determining the second model for the retention index may be conducted in one combined process sharing the corresponding steps.

After conducting the ensiling process in step S34, the procedure proceeds to step S35, where the silage product of the test samples is subjected to an analysis process in order to determine the dry matter content $DM_i$ of each test sample.

Then the method proceeds to step S37, where the dry matter contents $DM_i$ of the test silage products are correlated with the parameters $x_{i,e}$ determined in step S33 before ensiling. The correlation step may involve a mathematical regression analysis resulting in a mathematical function (including regression parameters) expressing the retention index number Rei as a function of the parameters $x_{i,e}$. In the present example, the inventors have used the same approach as describes with respect of FIG. 2 to adopt, a regression with the higher R-square value (cf. Eq. 2 above). Table 3 shows the regression parameters of the regression function of the second model obtained for the maize test samples.

TABLE 3

Regression coefficient of the second model for predicting the dry matter loss (values are calculated on % of Dry Matter basis) assuming index I1 as quality index QI as reference

| Parameters $x_{i,e}$ | Intercept 223.34276 | $D_i$ | $E_i$ |
|---|---|---|---|
| Dry matter (DM) | | −5.10303 | 0.06241 |
| Total Sugars (TS) | | −2.60745 | 0.13445 |
| ADLignine (ADL) | | −9.80569 | 0 |
| Starch (STA) | | −2.62779 | 0.02439 |
| NDF | | 0 | 0.00953 |
| ADF | | 0 | −0.0891 |

The regression function $Rei=f(x_{i,e})$ according to the second model using the regression coefficients of Table 3 can be thus expressed as follows (Eq. 2.1):

$$Rei=100-(223.34276-5.10303DM-2.60745TS-9.80569ADL-2.62779STA+0.06241DM^2+0.00953NDF^2-0.0891ADF^2+0.02439STA^2+0.13445TS^2)$$

The procedure of FIG. 3 thus ends in step S38 thus providing the second model Rei=f($x_{i,e}$) which can then be applied in the procedure of FIG. 1 for determining the expected dry matter loss of the new harvested maize during the ensiling process.

Figure 5:
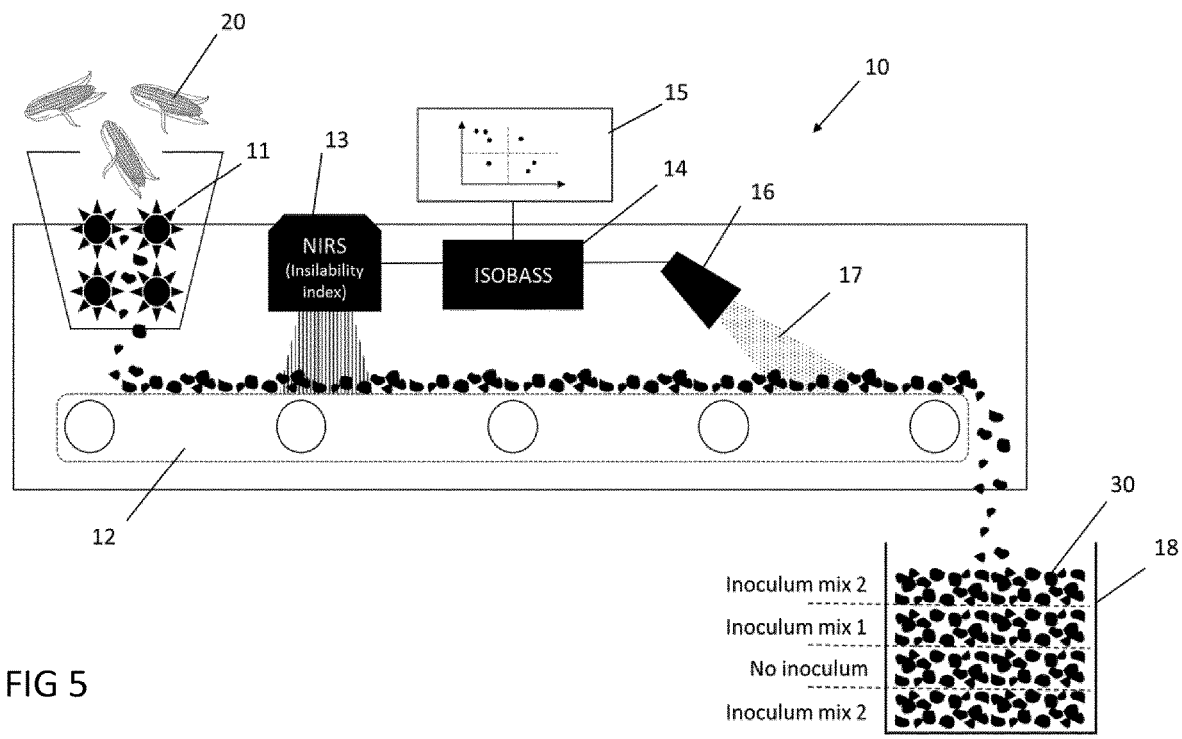
FIG. 5 schematic diagram of an apparatus for preparing a silage good according to a preferred embodiment of the invention.

Next, an apparatus for preparing a silage good having improved quality to be subjected to an ensiling process is described referring to FIG. 5.

The apparatus 10 comprises a filed chopper 11 for mechanically processing a freshly harvested good 20 in order to prepare particle sizes suitable to be subjected to ensiling. The apparatus further comprises a conveying belt 12 for transporting the harvested good to the various processing stations of the apparatus 10. The chopped harvested good 20 is thus transported by the conveying belt from the chopper 11 to analysing means 13 for analysing the freshly harvested and chopped good 20 in order to determine the plurality of parameters $x_i$ characterising a chemical composition and/or another property of the harvested good as described above. Here the analysing means 13 comprises a near infrared spectrometer NIRS. The NIRS radiates near infrared radiation of selected wavelengths to the chopped harvested good 20 and detects the corresponding absorbance or transmission. The apparatus 10 further comprises a computing station 14 connected to the analysing means 13 for analysing the NIR data submitted from the NIRS such as to determine the parameters $x_i$ from the NIR data. The computing station 14 further performs steps S14 to S16 of FIG. 1. For this purpose, the computing station 14 contains the first and the second model for determining the ensilability index number Ini and the retention index number Rei as a function of the parameters $x_i$. For example, the models may be stored in form of equations Eq. 1.1 and Eq. 2.1 as shown above in a computer-readable format. Furthermore, the computing station 14 includes an algorithm for determining the types $a_i$ and amounts m_$a_i$ of the ensiling additives to be supplied to the harvested good 20 depending on the ensilability index number Ini and the retention index number Rei as explained above. Optionally, the apparatus 10 may comprise displaying means 15 for displaying the result of the analysis, such as the determined indices Ini and Rei in form of the 2-dimensional representation shown in FIG. 4. The apparatus 10 further comprises supply means 16 such as spaying means for supplying ensiling additives 17 to the harvested good 20 according to types $a_i$ and amounts m_$a_i$ determined before. For this purpose, the harvested good 20 is further transported by the conveying belt 12 to the supply means 16, where the ensiling additive, particular inoculates of microorganisms, are sprayed on the harvested good thus obtaining the silage good 30. The silage good 30 may then be further transported by the conveying belt 12 to an ensiling tank 18, where the subsequent ensiling process is going to take place. As indicated in FIG. 5, the ensiling tank 18 is thus filled with different layers of the silage good 30 comprising different additives (if any), here selected from two inoculum mixes selected by the computing station 14 depending on the ensilability index number Ini and the retention index number Rei.

Figure 6:
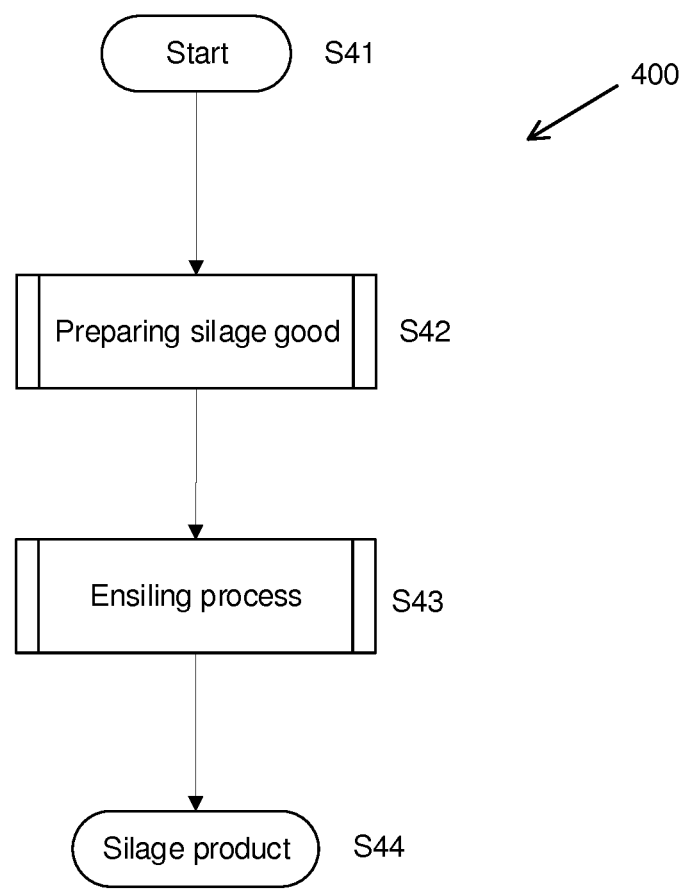
FIG. 6 flow chart of an ensiling process according to a preferred embodiment of the invention.

Next, the ensiling process 400 according to the invention is explained with reference to FIG. 6. The process starts in step S41 and proceeds to step S42, where a silage good 30 is prepared according to the invention. In other words, step S42 comprises steps S11 to S18 of the method 100 explained with reference to FIG. 1. After having prepared the silage good 30, the process proceeds to step S43 where the silage good is subjected to fermentation, i.e. ensiling, to obtain the desired silage product. The ensiling comprises commonly known microbiological fermentation processes. However, due to the preparation of the silage good according to the invention involving the supply of selected additives taking into account the composition of the harvested good, the ensiling process is improved compared to a process where no additives are supplied or where additives are supplied in a more intuitively manner. As result, a silage product of improved quality is yielded comprising higher amounts of nutrients for the animals to be fed and of dry matter.

REFERENCE SIGNS 10 apparatus for preparing a silage good
11 field chopper
12 conveying means, conveying belt
13 analysing means, NIRS
14 determination means, computing station
15 displaying means
16 supply means
17 ensiling additive
18 ensiling tank
20 harvested good
30 silage good
100 method of preparing silage good
200 method of obtaining first model applied in method 100
300 method of obtaining second model applied in method 100
400 ensiling process
Ini ensilability index number
Rei retention index number
$x_i$ parameters characterising chemical composition and/or property of the harvested good
$x_{i,e}$ parameters characterising chemical composition and/or property of the harvested test sample before ensiling
$y_{i,e}$ parameters characterising chemical composition and/or property of the test sample after ensiling
$a_i$ type of ensiling additive
m_$a_i$ amount of ensiling additive

The invention claimed is:
1. A method of preparing of a silage good having improved quality to be subjected to an ensiling process to produce a silage product, the method comprising:
selecting a freshly harvested good to be subjected to the ensiling process;
mechanically processing, via a first device, the freshly harvested good thereby reducing a particle size of the freshly harvested good;
determining, via an automated process, a plurality of parameters ($x_i$) characterising a chemical composition and/or a property of the harvested good;
applying a first model on the determined parameters (xi) to determine an ensilability index number (Ini), that is characteristic for an expected ensilability of the harvested good;
applying a second model on the determined parameters (xi) to determine a retention index number (Rei), that is characteristic for an expected loss of dry matter (DM) of the harvested good during the ensiling process;
predicting, based on the ensilability index number (Ini) and the retention index number (Rei), an expected quality of the silage product;

responsive to predicting the expected quality of the silage product, determining types and amounts of ensiling additives to be added to the harvested good for controlling the ensiling process depending on the ensilability index number (Ini) and the retention index number (Rei) by using a lookup table with a mapping between the types and amounts of ensiling additives and the ensilability index number (Ini) and the retention index number (Rei);

supplying the determined additives to the harvested good to obtain the silage good; and subjecting the silage good to the ensiling process to produce the silage product.

2. The method of claim 1, wherein the automated process comprises a spectroscopic method, a chromatographic method, thermal imaging methods, wet analysis, elemental trace analysis, or combinations thereof.

3. The method of claim 1, wherein the harvested good is selected from corn, sorghum, sugar cane, rye, *triticale*, barley, wheat, lolium, and alfalfa.

4. The method of claim 1, wherein the parameters (xi) are selected from a pH value, a water content, a dry matter (DM) content, an ash (A) content, an acid insoluble ash (AIA) content, a crude protein (CP) content, a total sugar (TS) content, a glucose (GLU) content, a fructose (FRU) content, a sacarose (SAC) content, a total ether extract (EE) content, a starch content, a cellulose content, a lignin content, a crude fibre (CF) content, an acid detergent fibre (ADF) content, a neutral detergent fibre (NDF) content, and an acid detergent lignin (ADL) content.

5. The method of claim 1, wherein the first model applied in the method is obtained by correlating parameters ($x_{i,e}$) measured from test samples before ensiling with the chemical composition of the obtained silage product after the ensiling at predetermined conditions.

6. The method of claim 1, wherein the second model applied in the method is obtained by correlating parameters ($x_{i,e}$) measured from test samples before ensiling with the dry matter content after the ensiling at predetermined conditions.

7. The method of claim 1, wherein the first and/or the second model applied in the method is/are obtained by mathematical regression analysis.

8. The method of claim 1, wherein the determination of types and amounts of ensiling additives to be added to the harvested good comprises:

comparing the ensilability index number (Ini) to a first threshold value ($Ini_1$) and depending on whether the determined ensilability index number (Ini) exceeds or falls below the first threshold value ($Ini_1$), the type and content of an additive selected from a first group of additives is determined; and comparing the retention index number (Rei) to a second threshold value ($Rei_1$) and depending on whether the determined ensilability index number (Rei) exceeds or falls below the second threshold value ($Rei_1$), the type and content of an additive selected from a second group of additives is determined.

9. The method of claim 8, wherein the first and second group of additives comprises inoculates of different bacterial strains, and wherein the different bacterial strains comprise *Lactobacillus Plantarum, Lactobacillus sasei, Streptococcus faecium, Pediococcus pentosaceus, Lactobacillus curbatus, Lactobacillus coryniformis* ssp. *coryniformis, Pediococcus acidilactici, Lactobacillus brevis, Lactobacillus buchneri, Lactobacillus fermentum, Lactobacillus viridescens, Lactobacillus rhamnosus, Leuconstoc cremoris*, or *Leuconstoc dextranicum*.

10. The method of claim 9, wherein the first group of additives comprises *Lactobacillus Plantarum, Lactobacillus sasei, Streptococcus faecium, Pediococcus pentosaceus, Lactobacillus curbatus, Lactobacillus coryniformis* ssp. *coryniformis, Pediococcus acidilactici*, and wherein the second group of additives comprises *Lactobacillus brevis, Lactobacillus buchneri, Lactobacillus fermentum, Lactobacillus viridescens, Lactobacillus rhamnosus, Leuconstoc cremoris*, and *Leuconstoc dextranicum*.

11. The method of claim 1, wherein the method is carried out in a continuous manner during harvesting the harvest good.

12. The method of claim 2, wherein the spectroscopic method comprises infrared spectroscopy, near infrared spectroscopy, terahertz spectroscopy, terahertz time-domain spectroscopy, Raman spectroscopy, ultraviolet spectroscopy, mass spectroscopy, MALDI-TOF spectroscopy, nuclear magnetic spectroscopy, or laser induced breakdown spectroscopy, and wherein the chromatographic method comprises gas chromatography or high-performance liquid chromatography.

13. The method of claim 3, wherein the corn is *Zea mays*, wherein the sorghum is *S. bicolor*, wherein the sugar cane is *Saccharum officinarum*, wherein the rye is *Secale cereale*, wherein the barley is *Hordeum vulgare*, wherein the wheat is *Triticum aestivum*, wherein the lolium is *Lolium perenne*, and wherein the alfalfa is *Medicago sativa*.

14. The method of claim 1, wherein the determination of the ensilability index number (Ini) and the retention index number (Rei) and the supplementation of the determined additives to the harvested good is conducted on a field as an in-line process with a harvest of the freshly harvested good for the silage good to be obtained on the field and directly provided to the ensiling process.

15. The method of claim 1, wherein the plurality of parameters ($x_i$) are determined simultaneously.

16. A method of preparing a silage good for production of a silage product, the method comprising:

selecting a freshly harvested good to be subjected to an ensiling process, wherein the harvested good is selected from corn, sorghum, sugar cane, rye, *triticale*, barley, wheat, lolium, and alfalfa;

mechanically processing, via a first device, the freshly harvested good thereby reducing a particle size of the freshly harvested good;

determining, via an automated process, a plurality of parameters ($x_i$) characterising a chemical composition and/or a property of the harvested good;

applying a first model on the determined parameters (xi) to determine an ensilability index number (Ini), that is characteristic for an expected ensilability of the harvested good;

applying a second model on the determined parameters (xi) to determine a retention index number (Rei), that is characteristic for an expected loss of dry matter (DM) of the harvested good during the ensiling process;

predicting, based on the expected ensilability and the expected loss of DM of the harvested good, an expected quality of the silage product;

responsive to predicting the expected quality of the silage product, determining types and amounts of ensiling additives to be added to the harvested good for controlling the ensiling process depending on the ensilability index number (Ini) and the retention index number (Rei) by using a lookup table with a mapping between the types and amounts of ensiling additives and the ensilability index number (Ini) and the retention index number (Rei), wherein the ensiling additives comprise one or more of *Lactobacillus Plantarum, Lactobacillus sasei, Streptococcus faecium, Pediococcus pentosaceus, Lactobacillus curbatus, Lactobacillus coryniformis* ssp. *coryniformis, Pediococcus acidilactici, Lactobacillus brevis, Lactobacillus buchneri, Lactobacillus fermentum, Lactobacillus viridescens, Lactobacillus rhamnosus, Leuconstoc cremoris, Leuconstoc dextranicum*, or combinations thereof;

spraying the harvested good with the determined additives to obtain the silage good; and subjecting the silage good to the ensiling process to produce the silage product.

* * * * *